United States Patent
Hartman et al.

(10) Patent No.: US 9,594,061 B2
(45) Date of Patent: Mar. 14, 2017

(54) METHODS AND APPARATUS FOR DETECTING DEFECTS IN AN OBJECT OF INTEREST

(71) Applicant: Orbital ATK, Inc., Dulles, VA (US)

(72) Inventors: John K. Hartman, Logan, UT (US); Lee H Pearson, Bear River City, UT (US)

(73) Assignee: Orbital ATK, Inc., Plymouth, MN (US)

( * ) Notice: Subject to any disclaimer, the term of this patent is extended or adjusted under 35 U.S.C. 154(b) by 422 days.

(21) Appl. No.: 14/178,100

(22) Filed: Feb. 11, 2014

(65) Prior Publication Data

US 2015/0226705 A1    Aug. 13, 2015

(51) Int. Cl.
*G01N 29/11* (2006.01)
*G01N 29/22* (2006.01)
*G01N 29/265* (2006.01)
*G01N 29/34* (2006.01)
*G01N 29/44* (2006.01)

(52) U.S. Cl.
CPC ............ *G01N 29/11* (2013.01); *G01N 29/225* (2013.01); *G01N 29/265* (2013.01); *G01N 29/343* (2013.01); *G01N 29/348* (2013.01); *G01N 29/4454* (2013.01)

(58) Field of Classification Search
USPC ............. 324/209, 693, 699, 633–644, 71, 1; 73/606, 632, 583, 588, 633, 649, 763, 73/1.82, 703, 627–630; 702/35; 60/253
See application file for complete search history.

(56) References Cited

U.S. PATENT DOCUMENTS

| 4,976,150 A * | 12/1990 | Deka | G01N 29/2437 |
| | | | 73/644 |
| 5,305,239 A * | 4/1994 | Kinra | G01H 5/00 |
| | | | 702/39 |
| 5,309,765 A * | 5/1994 | Horigome | G01N 29/11 |
| | | | 73/602 |
| 5,847,394 A * | 12/1998 | Alfano | A61B 1/042 |
| | | | 250/341.1 |
| 2002/0116141 A1* | 8/2002 | Mo | G01S 7/52026 |
| | | | 702/76 |

(Continued)

OTHER PUBLICATIONS

Ultrasonic Inspection Method for Solid Rocket Motor; Kurabayashi et al. , IHI Aerospace Co. Ltd., Japan, Jun. 2010.*

(Continued)

*Primary Examiner* — Melissa Koval
*Assistant Examiner* — Nasima Monsur
(74) *Attorney, Agent, or Firm* — TraskBritt

(57) ABSTRACT

A method for detecting defects in an object of interest comprises applying an ultrasonic signal including a tone burst having a predetermined frequency and number of cycles into an object of interest, receiving a return signal reflected from the object of interest, and processing the return signal to detect defects in at least one inner material. The object may have an outer material and the at least one inner material that have different acoustic impedances. An ultrasonic sensor system includes an ultrasonic sensor configured to generate an ultrasonic signal having a tone burst at a predetermined frequency corresponding to a resonant frequency of an outer material of an object of interest.

20 Claims, 5 Drawing Sheets

(56) References Cited

U.S. PATENT DOCUMENTS

2008/0285881 A1* 11/2008 Gal .......................... G06T 5/20
                                                          382/261
2009/0223295 A1*  9/2009 Kondo ................. G01N 29/043
                                                           73/627

OTHER PUBLICATIONS

Ultrasonic Inspection Method for Solid Rocket Motor;http:// www.ndt.net/search/docs.php3?showform=off&id=8878.*

* cited by examiner

METHODS AND APPARATUS FOR DETECTING DEFECTS IN AN OBJECT OF INTEREST

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. NNM07AA75C awarded by NASA.

TECHNICAL FIELD

Embodiments of the present disclosure relate to detection of defects in an object using an ultrasonic sensor. In particular, embodiments relate to a method of detection of defects in materials located behind a higher acoustic impedance material, and to apparatus configured to implement the method.

BACKGROUND

Conventional nondestructive evaluation (NDE) techniques have been used in the Space Shuttle program to screen for defects (e.g., cracks, debond, voids, etc.) in the basic case, insulation, propellant assembly of the solid rocket motor. Uncertainty in the size, location, and orientation of defects may result in uncertainty in the analytical models (i.e., constitutive models) designed to assess structural allowable stresses and strains for the propellant. Defects that occur in propellant-liner interface may cause hot gas to be present near the wall of the rocket motor case. In addition, if a defect near the liner extends further into the propellant, the propellant may become detached from the bonding surface of the liner. Debonding may cause further defects (e.g., cracks) in the propellant, which may result in augmented and accelerated burning of the propellant, including near the wall of the case, as well as concerns regarding the structural impact of the decreased bonding with the liner.

In addition, environmental factors (e.g., moisture) may weaken the adhesion strength of the propellant binder to the surface of the reinforcing and combustible fillers in the solid rocket motor over time, which can result in reduced load bearing capability of the propellant. Because there is often uncertainty associated with the constitutive properties of the these polymeric systems especially when exposed to environmental aging, the term "health" of solid rocket motor is sometimes used to classify the launch readiness of the solid rocket motor and the propellant's ability to withstand damage during the dynamic launch event.

Conventional methods for screening the health of a solid rocket motor include radiographic (e.g., X-ray) inspection methods for verifying the health and quality of the propellant, liner, and insulation of a solid rocket motor. For example, FIG. 1 is a cut-out side view of a solid rocket motor 100 including a case 106 and propellant 108. Additional insulation materials may be located between the case 106 and the propellant 108. FIG. 1 shows the solid rocket motor 100 undergoing screening using conventional X-ray methods. For example, a first X-ray device 110 may be oriented such that the X-ray 112 may be transmitted substantially orthogonally to the solid rocket motor 100 to obtain an X-ray image through a thickness of the solid rocket motor 100 and into the propellant 108. As a result, defects in the propellant 108 may be detected. A second X-ray device 120 may be oriented at an angle such that the second X-ray device 120 obtains a tangential image of the solid rocket motor 100 to better detect defects in the additional insulation layers that largely go undetected by the first X-ray device 110.

Because of the size of solid rocket motors, this inspection method may require an undesirably large number of man-hours to obtain the images. In particular, the tangential image may be a very small field of view relative to the entire solid rocket motor 100 being imaged. As a result, after each tangential image is obtained, the solid rocket motor 100 may be rotated to a new position to obtain another tangential image. Each tangential image may require a substantial number of man hours to rotate the solid rocket motor 100 between each image, in addition to the time that is needed to expose the solid rocket motor 100 to an X-ray 122. Thus, although conventional inspection methods may have resulted in the detection of defects, the conventional inspection methods may be time consuming and costly.

Some additional conventional inspection approaches have attempted to detect voids using ultrasonic methods. These conventional ultrasonic methods have used either a repetitive high frequency (e.g., 1 MHz to 10 MHz) square or instantaneous pulse for the ultrasonic signal propagating into a material, and measuring and quantifying discreet reflections off of internal interfaces or potential defects. Images may be generated based on the peak amplitude responses from the ultrasonic signal. The conventional inspection methods, however, have not adequately provided the necessary depth to obtain accurate information any significant distance past the inside wall of case 106. Therefore, defects in the insulation materials may be undetected.

BRIEF SUMMARY

In some embodiments, the present disclosure comprises a method for detecting defects in an object of interest. The method comprises applying an ultrasonic signal including a tone burst having a predetermined frequency and number of cycles into an object of interest, the object having an outer material and at least one inner material that have different acoustic impedances, receiving a return signal reflected from the object of interest, and processing the return signal to detect defects in the at least one inner material.

In other embodiments, the present disclosure comprises an ultrasonic sensor system, including an ultrasonic sensor configured to generate an ultrasonic signal having a tone burst at a predetermined frequency corresponding to a resonant frequency of an outer material of an object of interest.

DETAILED DESCRIPTION

Figure 1:
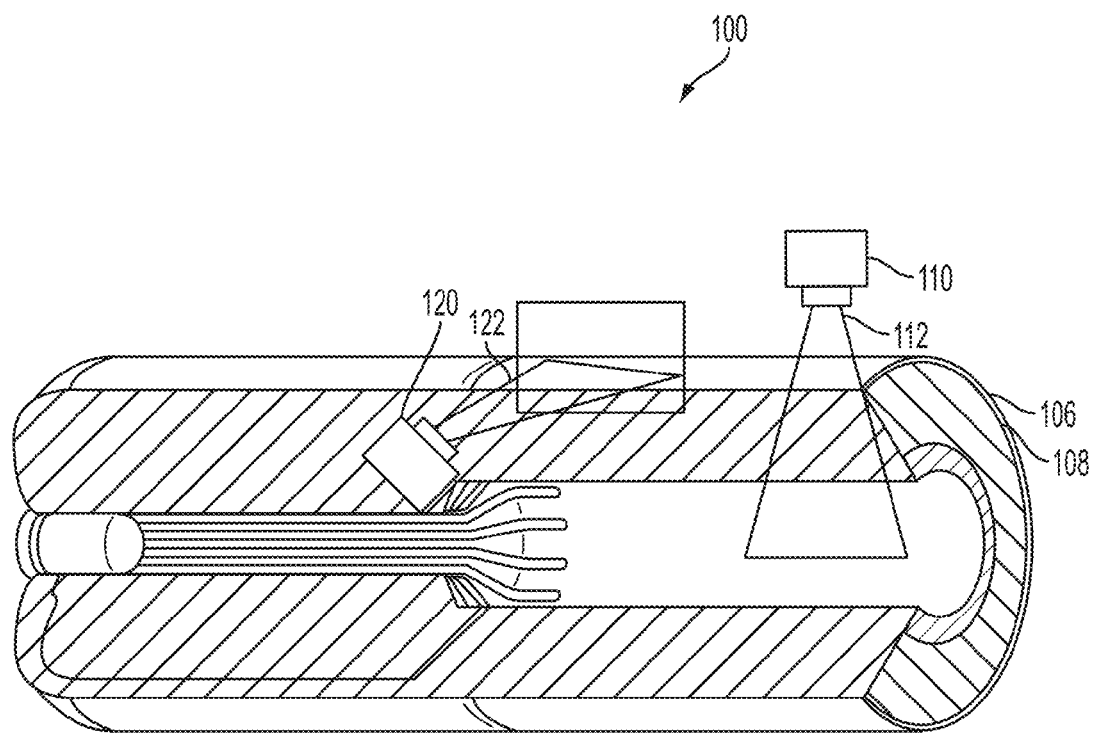
FIG. 1 is a cut-out side view of a solid rocket motor including a case and propellant.

In the following description, reference is made to the accompanying drawings in which is shown, by way of illustration, specific embodiments of the present disclosure. Other embodiments may be utilized and changes may be made without departing from the scope of the disclosure. The following detailed description is not to be taken in a limiting sense, and the scope of the present invention is defined only by the appended claims.

Furthermore, specific implementations shown and described are only examples and should not be construed as the only way to implement or partition the present disclosure into functional elements unless specified otherwise herein. It will be readily apparent to one of ordinary skill in the art that the various embodiments of the present disclosure may be practiced by numerous other partitioning solutions.

In the following description, elements, circuits, and functions may be shown in block diagram form in order not to obscure the present disclosure in unnecessary detail. Additionally, block definitions and partitioning of logic between various blocks is exemplary of a specific implementation. It will be readily apparent to one of ordinary skill in the art that the present disclosure may be practiced by numerous other partitioning solutions. Those of ordinary skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the present disclosure may be implemented on any number of data signals including a single data signal.

The various illustrative logical blocks, modules, and circuits described in connection with the embodiments disclosed herein may be implemented or performed with a general-purpose processor, a special-purpose processor, a Digital Signal Processor (DSP), an Application-Specific Integrated Circuit (ASIC), a Field-Programmable Gate Array (FPGA) or other programmable logic device, a controller, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A general-purpose processor may be considered a special-purpose processor while the general-purpose processor executes instructions (e.g., software code) stored on a computer-readable medium. A processor may also be implemented as a combination of computing devices, such as a combination of a DSP and a microprocessor, a plurality of microprocessors, one or more microprocessors in conjunction with a DSP core, or any other such configuration.

Also, it is noted that the embodiments may be described in terms of a process that may be depicted as a flowchart, a flow diagram, a structure diagram, or a block diagram. Although a process may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on computer-readable media. Computer-readable media includes both computer storage media and communication media, including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed or that the first element must precede the second element in some manner. In addition, unless stated otherwise, a set of elements may comprise one or more elements.

As used herein, the term "sensor" may be used interchangeably with "transducer." As used herein, both sensor and transducer are intended to refer to an object that may be configured to perform conversion of energy from one form to another (i.e., be energized to generate an ultrasonic signal), detect the return signal, transmit information regarding the return signal to the control system, and combinations thereof.

Embodiments of the present disclosure comprise detecting defects in a material of interest using an ultrasonic approach. Although many of the examples described herein refer to a solid rocket motor and its components, embodiments of the present disclosure are not so limited. A solid rocket motor is used merely as an example of one object (such term, as used herein, meaning and including assemblies comprising multiple components, materials, or both) that may be desirable for investigation of defects using the embodiments of this disclosure. Therefore, discussion of a solid rocket motor having one or more different parts (e.g., case, insulation, liner, propellant, etc.) is applicable more generally to any object (e.g., space launch systems, tanks, armor, etc.) that includes multiple materials with different acoustic impedances—particularly if there is an acoustic impedance mismatch between an outer layer having a higher acoustic impedance relative to the inner layer(s). For example, a steel case has a high acoustic impedance relative to rubber. The greater the impedance mismatch (i.e., differential) between two materials, the worse conventional inspection methods tend to perform in detecting defects associated with the inner materials because more acoustic energy stays trapped in the outer layer and/or the acoustic energy is quickly attenuated in the inner layers.

Figure 2:
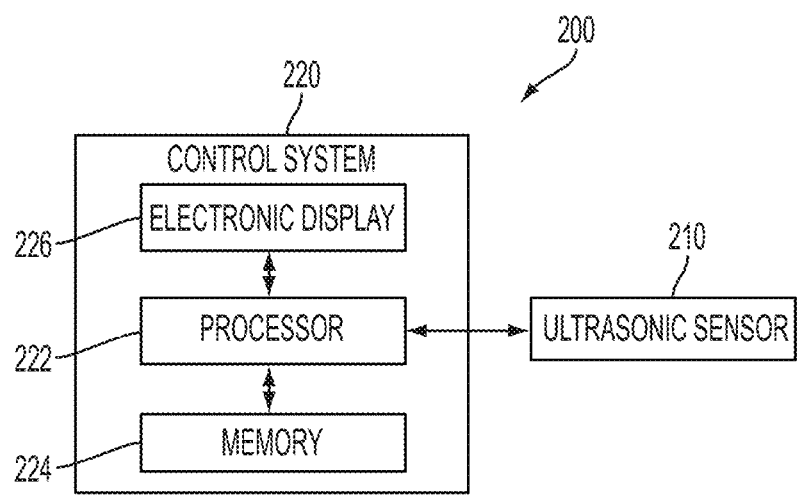
FIG. 2 is an ultrasonic sensor system according to an embodiment of the present disclosure.

FIG. 2 is a simplified schematic diagram of an ultrasonic sensor system 200 according to an embodiment of the present disclosure. The ultrasonic sensor system 200 may include a control system 220 operably coupled with an ultrasonic sensor 210. The control system 220 may include a processor 222 operably coupled with a memory 224 and an electronic display 226. The memory 224 may be configured to store instructions for execution by the processor 222 to control the ultrasonic sensor 210 and process received data as described herein. The memory 224 may also be configured to store the data associated with the ultrasonic sensor 210. The electronic display 226 may be configured to display the data (e.g., as a graph, image, etc.) for the technician to view and interpret. Operation of the ultrasonic sensor system 200 will be further described with reference to the figures below.

Figure 3:
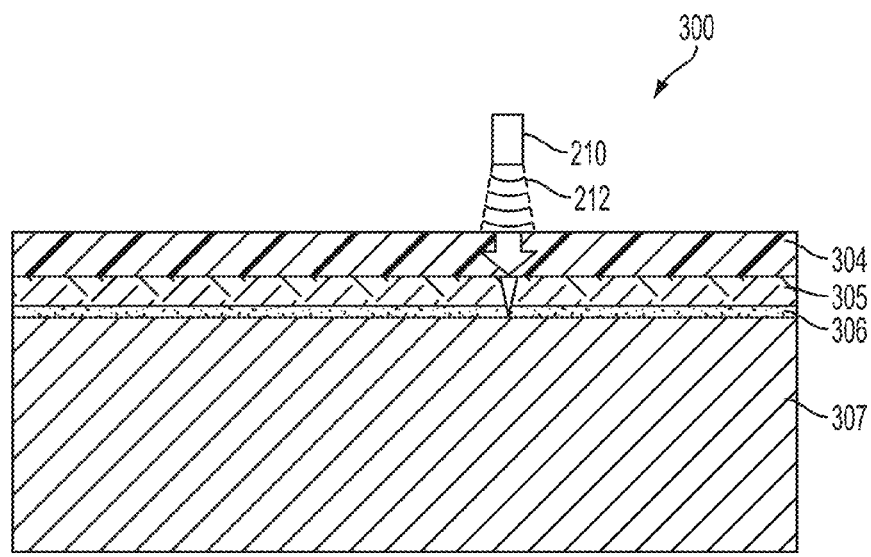
FIG. 3 is a cross section of a solid rocket motor that may be inspected by the ultrasonic sensor.

FIG. 3 is a cross section of a solid rocket motor 300 that may be inspected by the ultrasonic sensor 210. The solid rocket motor 300 may include a plurality of materials 304, 305, 306, 307 having different acoustic impedances. For example, in the solid rocket motor 300, the outer material may be a case 304, the next material may be an insulation material 305, the next material may be a liner 306, and the final, innermost material may be propellant 307. The case 304 may be formed from steel or other appropriate materials, which may include metals, metal-alloys, and carbon or other fiber reinforced plastic materials. The insulation material 305 may include Nitrile Butadiene Rubber (NBR), Room Temperature Vulcanized (RTV) Rubber, Silicone Rubber, ethylene propylene diene Monomer (EPDM) Rubber, Urethane Rubber, Hydroxy Terminated Polybutidiene (HTPB) Rubber, Inorganic Phosphazene Rubbers, Natural Rubber, or other suitable insulation materials. The liner may 306 be formed from materials such as a polyurethane adhesive, and the like. Propellants 307 of solid rocket motors may include combustive and particulate materials mixed within an elastomeric binder material (e.g., HTPB, Polybutadiene/Acrylonitrile (PBAN), or Nitrate ester/polyester (NEPE) based polymers).

In operation, the ultrasonic sensor 210 may interrogate the solid rocket motor 300 to detect defects by applying an ultrasonic signal 212 to the solid rocket motor 300. Applying the ultrasonic signal 212 may include energizing the ultrasonic sensor 210 to generate a tone burst having a predetermined frequency that is tuned to create a standing wave (i.e., destructive interferences) in the reflections within the case 304. With a tone burst, the ultrasonic signal 212 is driven for a predetermined number of cycles (e.g., 5 cycles) and then the ultrasonic signal 212 is shut off. Within the tone burst, the ultrasonic signal 212 may be a sine wave, square wave, or other periodic signal having the predetermined frequency band to create a standing wave in the case 304. With the reflections in the case 304 destructively interfering with themselves, the smaller energy reflections from the deeper internal layers (e.g., insulation 305, liner 306, propellant 307) may have a higher signal to noise ratio (SNR) enabling their detection. The predetermined frequency may be approximately the resonant frequency for the case 304 that is based, at least in part, on the material of the case 304 and the thickness of the case 304. For example, for a steel case 304 that is approximately 0.5-inch thick, the predetermined frequency may be tuned to be approximately 250 kHz, which is approximately the frequency at which the wavelength is about twice the thickness of the case 304. As a result, the effects of the reflections within the case 304 may be reduced so that the return signal coming back from the internal layers (e.g., insulation, liner) may be more detectable. Because the predetermined frequency of the ultrasonic signal 212 may be tuned to the resonant frequency of the case 304 (or other outer material), which resonant frequency is dependent on the thickness of the material used, having a substantially uniform thickness for the case 304 may improve results. In some embodiments, the thickness of the other materials (e.g., insulation, liner) may vary without significantly affecting the results.

In addition, because lower frequencies (e.g., in the kHz range) may be used in implementation of embodiments of the disclosure in comparison to those employed in conventional methods, more energy may pass through deeper into the internal layers of the solid rocket motor 300 such that a deeper image may be obtained. As a result, the ultrasonic signal 212 may experience less attenuation in the internal layers so that information about the conditions of defects deeper into the solid rocket motor 300.

Figure 4:
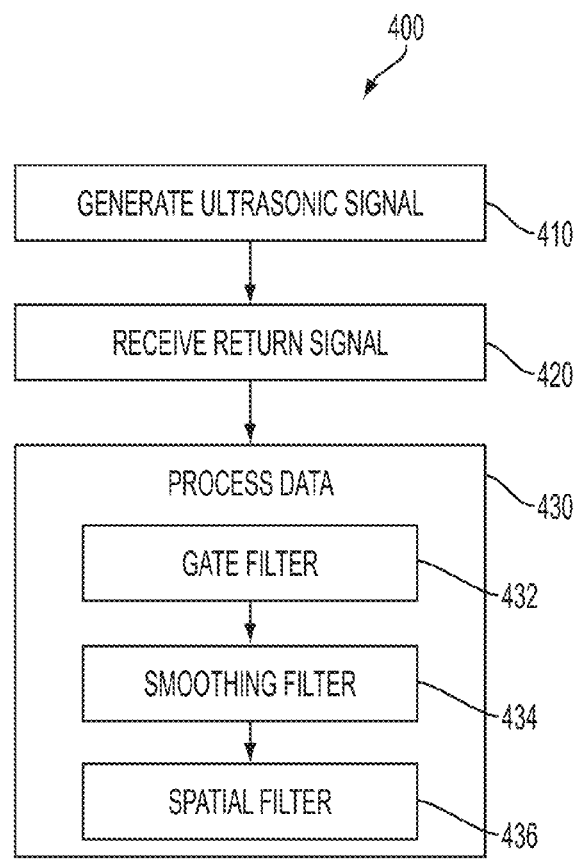
FIG. 4 is a flow chart illustrating a method of detecting defects in an object using an ultrasonic sensor according to an embodiment of the present disclosure.

FIG. 4 is a flow chart 400 illustrating a method of detecting defects in an object using an ultrasonic sensor according to an embodiment of the present disclosure. At operation 410, the ultrasonic signal may be generated, such as by an ultrasonic sensor 210 (FIGS. 2, 3). As discussed above, the ultrasonic signal may include a tone burst that is generated for a predetermined number of cycles (e.g., five cycles) before being shut off. In addition, the frequency of the ultrasonic signal may be set at approximately the resonant frequency of the outer material (e.g., case of a solid rocket motor) so that a standing wave may be formed in the outer material of the object being interrogated.

At operation 420, the return signals from the different reflections may be received. After the tone burst is shut off, there may be a greater opportunity to detect the reflections from the deeper internal layers because the reflections within the case of the outer material destructively interfere due to the predetermined frequency being tuned to the resonance of the outer material.

At operation 430, the data may be processed to detect the defects. Processing the data may include one or more filters on the data (e.g., operations 432, 434, 436).

At operation 432, a gate filter may be applied. The "gate" filter refers to applying the ratio of the gate periods that will be discussed more fully below with respect to FIG. 5. The gate filter may include summing the energy from the return signal during a gate period occurring after the tone burst has been shut off, and dividing that sum by the sum of the energy from the return signal during another gate period occurring during the tone burst. The resulting ratio may then be assigned as the value of the pixel corresponding to that waveform. The summing may include averaging the energy during the corresponding gate period, such as by taking the root-mean-square (RMS) of the energy during the corresponding gate period. The resulting RMS ratio may cause the image to be less sensitive to individual maximum points within the gate, which could be more easily affected by factors other than actual defects (e.g., case wall thickness changes), and also less sensitive to variations in signal strength due to small changes in ultrasonic sensor orientation because of sensor drag.

At operation 434, a smoothing filter may be applied. The smoothing filter refers to the processor smoothing the data by taking an average value from neighboring pixels. For example, a 3×3 Gaussian smoothing function may be applied that takes an average of each 3×3 block of pixels and assigns the average value of the 3×3 block to the pixel in the center. Thus, each pixel of the resulting image may be an average of the each of its surrounding pixels. The resulting image from operation 434 may remove some of the random and systematic error, such as the streakiness in the data (e.g., due to small changes in ultrasonic sensor orientation because of sensor drag); however, some of the sharpness of the image may also be reduced.

At operation 436, a spatial filter may be applied. The spatial filter may be configured to flatten the image if the data slowly changes from pixel to pixel producing slowly varying gradients. If, however, there are sudden changes in the pixel values, the spatial filter may accentuate the pixel values. As a result, the sudden changes in the data become enhanced or more pronounced in the final image. As these sudden changes in the data correspond to the edges of defects in the object, the detection of these defects may be improved.

Figure 5:
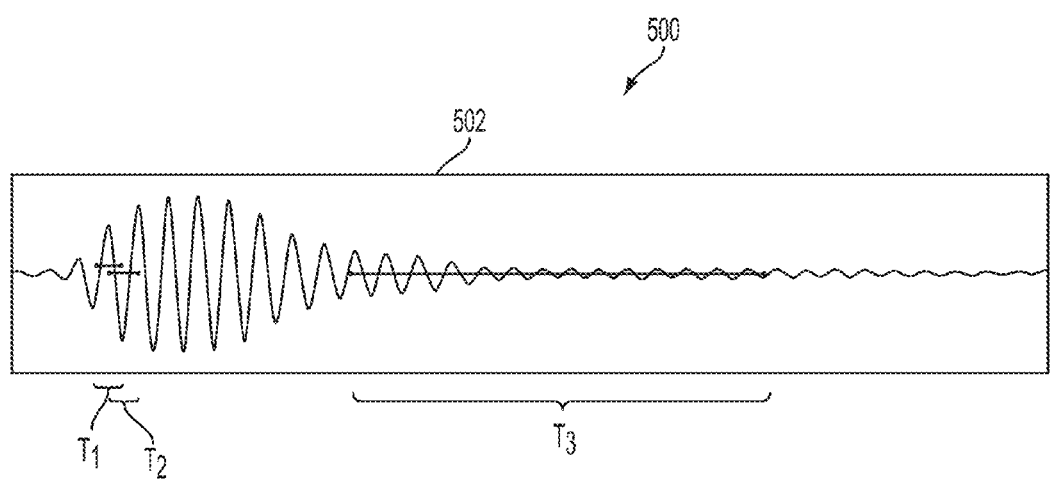
FIG. 5 is a waveform of the return signal received by the ultrasonic sensor for an individual pixel of a greater image.
Figures 6A, 6B, 6C:
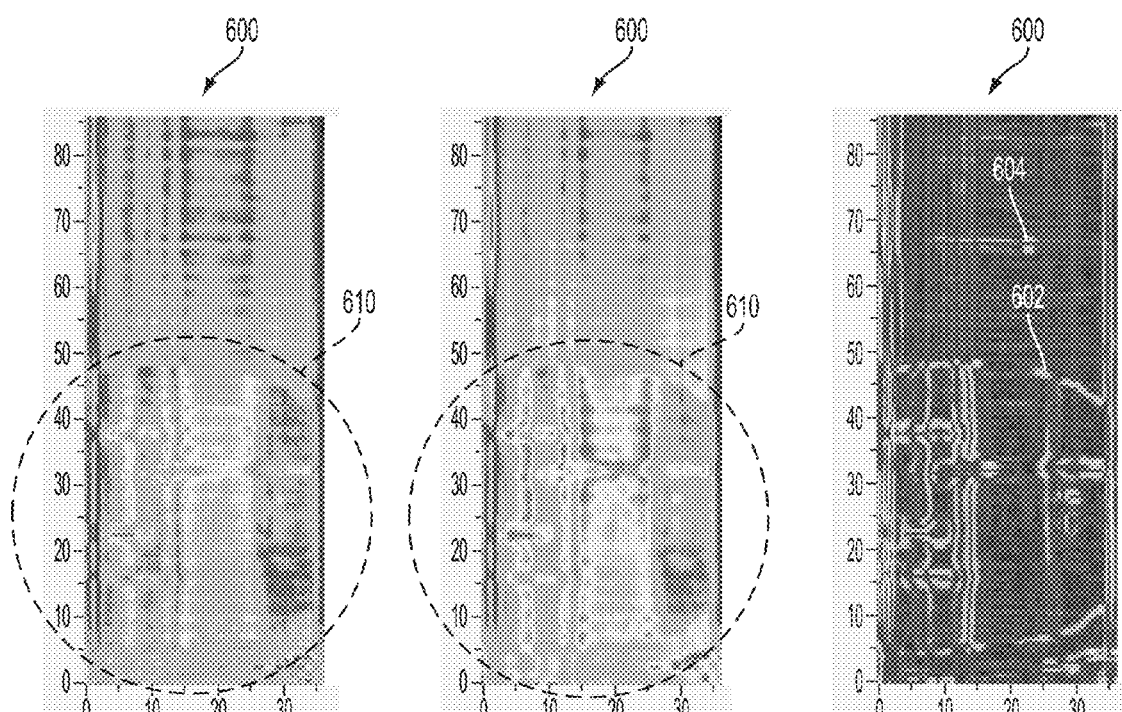
FIGS. 6A-6C are resulting processed images of an inspection of an object for defects according to an embodiment of the present disclosure.

FIG. 5 is a waveform 500 of a return signal 502 received by the ultrasonic sensor for an individual pixel of a greater image (e.g., FIGS. 6A-6C). The ultrasonic sensor may be supported by a scanner such that the ultrasonic sensor may scan from location to location across an area of the object of interest. At each location of the ultrasonic sensor, such a return signal 502 may be received to obtain information for the additional pixels of the resulting image.

As shown in FIG. 5, the amplitude of the return signal 502 may be greater at the beginning of the return signal 502, which corresponds to the tone burst of the ultrasonic signal applied by the ultrasonic sensor and reflecting back from the front surface of the case wall. As the ultrasonic signal is shut off after the tone burst, the return signal 502 may begin to attenuate. Because the reflections within the case create destructive interferences (due to the frequency being substantially equal to the resonant frequency of the case), the return signal 502 received after the tone burst may be largely attributed to the reflections occurring within the inner layers of the solid rocket motor.

FIG. 5 also shows three "gate periods" that may be used during the processing of the return signal 502. As discussed above with respect to FIG. 4, the return signal 502 may be filtered to generate the value for the pixel associated with an individual waveform. A first gate period ($T_1$) begins at an approximate time at which the tone burst is applied to the solid rocket motor. A second gate period ($T_2$) may begin at a predetermined time after the first gate period ($T_1$) begins. The second gate period ($T_2$) is within the time that the tone burst is being generated. A third gate period ($T_3$) may begin at another predetermined time after the first gate period ($T_1$) begins. The third gate period ($T_3$) is within the time that the tone burst has been shut off, during which time the return signal 502 may be largely attributed to the reflections occurring within the inner layers of the solid rocket motor. Thus, the first gate period (T1) may act as a reference for when the second gate period ($T_2$) and third gate period ($T_3$) are to begin.

The durations of the second gate period ($T_2$) and third gate period ($T_3$) may be any desired duration so long as an accurate RMS average may be obtained. As discussed above, the gate filter may obtain a ratio of the summed energy (e.g., RMS average) during the third gate period ($T_3$) divided by the summed energy (e.g., RMS average) during the second gate period ($T_2$). This ratio value may be assigned to the pixel (i.e., data point) in the resulting image, which may further be processed according to other filters as desired.

FIGS. 6A-6C are resulting processed images 600 of an inspection of an object for defects according to an embodiment of the present disclosure. In FIGS. 6A-6C, the resulting image 600 comprises an array of pixels, wherein each pixel has a value that was obtained as discussed above with respect to FIGS. 4 and 5. In particular, the return signal 502 of FIG. 5 may undergo one or more filters to obtain a value for that pixel. The ultrasonic sensor may then scan to another location to obtain a value for another pixel, and so on.

For example, in FIG. 6A, the pixels of the image 600 may have undergone the gate filter (e.g., operation 432 of FIG. 4), which may result in the pixels being raw data represented as an RMS ratio of the returning signal during a time period after the tone burst and another time period occurring during the tone burse. Pixels within a region 610 may appear accentuated (e.g., as if one were to look through a drop of water), which may indicate a defect (e.g., an unbond between the liner and propellant). In FIG. 6B, the pixels of the image 600 may have undergone the smoothing filter (e.g., operation 434 of FIG. 4), which may result in each pixel being averaged with its surrounding neighboring pixels. As a result, the image 600 may appear less sharp but some of the streakiness in the data may be removed. In FIG. 6C, the pixels of the image 600 may have undergone the spatial filter (e.g., operation 436 of FIG. 4), which may result in each pixel being flattened (e.g., Sobel filter) to accentuate the edges of defects and enhance sudden changes.

Defects may be detected from the data by identifying sudden changes (e.g., contrasts) in the images of the energy of the return signals received by the ultrasonic sensor. For example, the edges of a first defect 602 (e.g., unbond) and a second defect 604 (e.g., void) may be accentuated so that such defects 602, 604 may be more easily detected. Some known changes may be ignored, such as the lines extending up and down the image 600. With solid rocket motors, such lines may simply correspond to overlaps in the insulation (e.g., changes in insulation thickness), which overlaps may be acceptable rather than being a critical defect of concern. The existence of such lines may be recognized, but ignored by the technician in appropriate instances.

Figure 7:
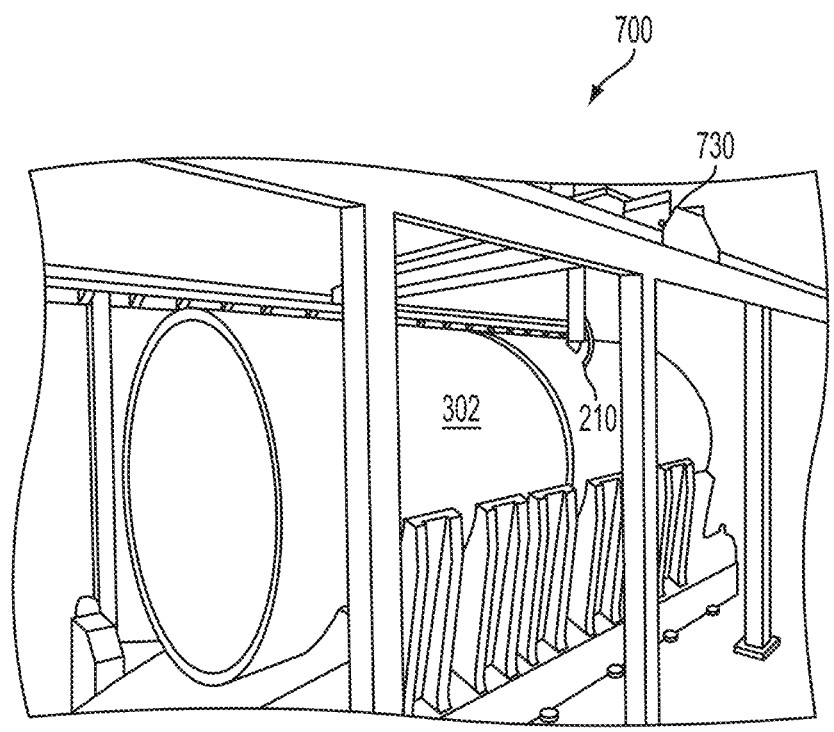
FIG. 7 is an ultrasonic sensor system configured to detect defects in an object according to an embodiment of the present disclosure.

FIG. 7 is an ultrasonic sensor system 700 configured to detect defects in an object (e.g., solid rocket motor 302) according to an embodiment of the present disclosure. The ultrasonic sensor system 700 may include a gantry 730 that controls the movement of the ultrasonic sensor 210 to interrogate the solid rocket motor 302. The gantry 730 may include a stationary frame that supports the ultrasonic sensor 210 as the ultrasonic sensor 210 is moved along the surface of the solid rocket motor 302 as defects are detected.

Figure 8:
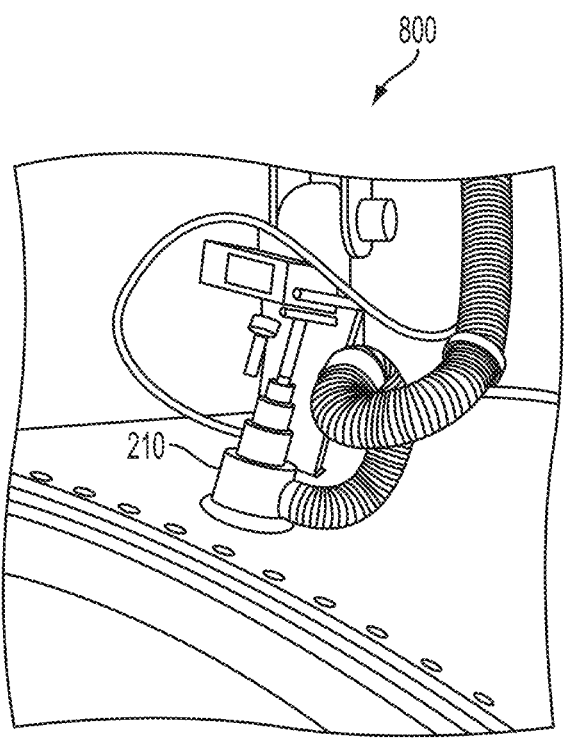
FIG. 8 is a close up view of the ultrasonic sensor of FIG. 7.

FIG. 8 is a close up view of the ultrasonic sensor 210 of FIG. 7. The ultrasonic sensor 210 may include a vacuum bell that utilizes liquid (e.g., water) as a couplant for the ultrasound signal. For example, the ultrasonic sensor 210 may be configured to fill an inner cavity within the head with water so that the ultrasonic signal passes through the water first, and then into the case.

Figure 9:
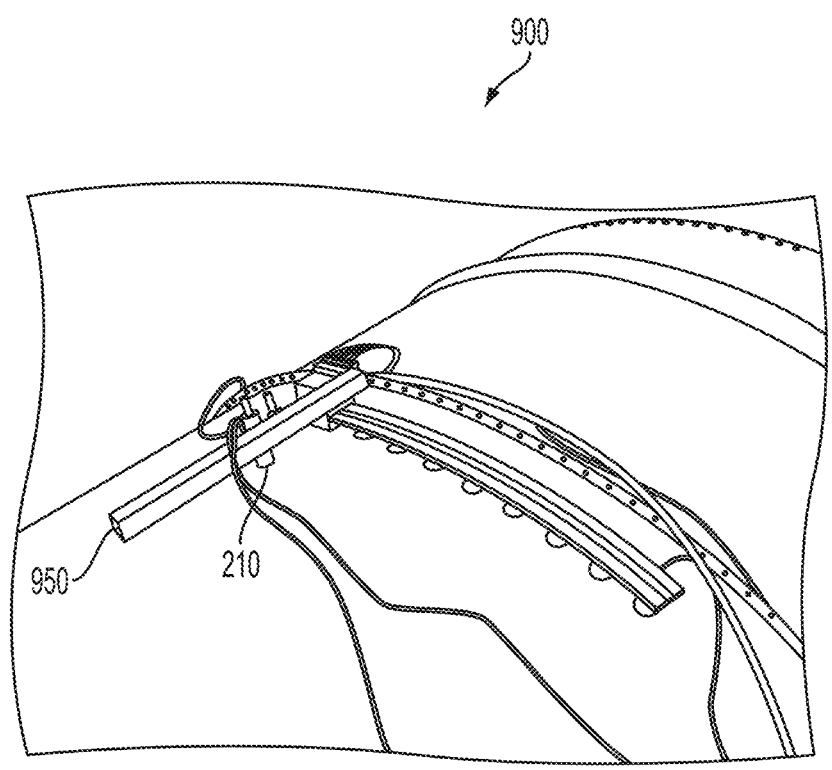
FIG. 9 is an ultrasonic sensor system configured to detect defects in an object according to an embodiment of the present disclosure.

FIG. 9 is an ultrasonic sensor system 900 configured to detect defects in an object (e.g., solid rocket motor 302) according to an embodiment of the present disclosure. The ultrasonic sensor system 900 may include a flexible track that couples to the solid rocket motor 302, and along which the ultrasonic sensor 210 may move in both the X- and the Y-direction. As a result, the ultrasonic sensor system 900 may be configured as a portable system, which may produce images on a smaller scale than the gantry 730 of FIG. 7.

While particular embodiments of the disclosure have been shown and described, numerous variations and alternate embodiments encompassed by the present disclosure will occur to those skilled in the art. Accordingly, the invention is only limited in scope by the appended claims and their legal equivalents.

What is claimed is:

1. A method for detecting defects in an object of interest, the method comprising:
 applying an ultrasonic signal including a tone burst having a predetermined frequency and number of cycles into an object of interest, the object having an outer material and at least one inner material that have different acoustic impedances, including setting the predetermined frequency of the tone burst at a resonant frequency of the outer material to create a standing wave in the outer material of the object of interest;

receiving a return signal reflected from the object of interest; and processing the return signal to detect defects in the at least one inner material.

2. The method of claim 1, wherein the outer material has an acoustic impedance that is higher than an acoustic impedance of the at least one inner material.

3. The method of claim 1, wherein applying the ultrasonic signal into an object of interest includes applying the ultrasonic signal into a solid rocket motor from a location exterior thereto, wherein the outer material includes a case and the at least one inner material includes a liner bonded between the case and propellant.

4. The method of claim 1, wherein processing the return signal includes filtering the return signal.

5. The method of claim 4, wherein filtering the return signal includes:
summing a first portion of the return signal received while the tone burst is being generated;
summing a second portion of the return signal received after the tone burst is finished being generated; and
calculating a ratio that includes the second portion divided by the first portion to assign a value to a pixel of a resulting image.

6. The method of claim 5, wherein summing the first portion and summing the second portion includes averaging energy from the first portion and averaging energy from the second portion, respectively.

7. The method of claim 6, wherein averaging energy includes calculating a root-mean-squared value for the energy.

8. The method of claim 4, wherein filtering the return signal includes performing a smoothing filter operation on the return signal.

9. The method of claim 4, wherein filtering the return signal includes performing a spatial filter operation on the return signal.

10. The method of claim 1, further comprising scanning an ultrasonic sensor across an area of the object of interest, wherein applying the ultrasonic signal, receiving the return signal, and processing the return signal are performed for every data point.

11. An ultrasonic sensor system, including:
an ultrasonic sensor configured to:
generate an ultrasonic signal having a tone burst at a predetermined frequency corresponding to a resonant frequency of an outer material of an object of interest having an outer material and at least one inner material that have different acoustic impedances wherein the predetermined frequency of the tone burst is set at a resonant frequency of the outer material of the object of interest to create a standing wave in the outer material of the object of interest.

12. The ultrasonic sensor system of claim 11, wherein the tone burst includes a square wave that has a predetermined number of cycles before being shut off.

13. The ultrasonic sensor system of claim 11, wherein the tone burst includes a sine wave that has a predetermined number of cycles before being shut off.

14. The ultrasonic sensor system of claim 11, further including a control system operably coupled to the ultrasonic sensor, the control system including a processor, a memory, and an electronic display.

15. The ultrasonic sensor system of claim 14, wherein the processor is programmed to filter a return signal received by the ultrasonic sensor to generate a pixel value associated with the return signal.

16. The ultrasonic sensor system of claim 15, wherein the processor is programmed to filter the return signal by taking a ratio of a summed energy received during a first gate period divided by summed energy received during a second gate period.

17. The ultrasonic sensor system of claim 16, wherein the first gate period occurs after the tone burst has been shut off, and the second gate period occurs during the tone burst.

18. The ultrasonic sensor system of claim 14, further including a scanning device supporting the ultrasonic sensor, and configured to scan the ultrasonic sensor across the object of interest.

19. The method of claim 1, wherein processing the return signal includes:
generating ratio values from a first summed energy detected during the tone burst and second summed energy detected after the tone burst as stopped; and
constructing a resulting image assigning the ratio values to pixel values of the resulting image.

20. The method of claim 19, wherein constructing the resulting image includes filtering the resulting image by smoothing the pixel values with data points.

* * * * *